(12) United States Patent
Obst et al.

(10) Patent No.: US 11,523,932 B2
(45) Date of Patent: Dec. 13, 2022

(54) ENTERIC FISTULA, RECTOVAGINAL FISTULA, AND OSTOMY EFFLUENT CONTAINMENT SYSTEM, AND DEVICES AND METHODS THEREOF

(71) Applicants: Andrew Thomas Obst, Scandia, MN (US); Maryanne Ruth Obst, Scandia, MN (US)

(72) Inventors: Andrew Thomas Obst, Scandia, MN (US); Maryanne Ruth Obst, Scandia, MN (US)

(*) Notice: Subject to any disclaimer, the term of this patent is extended or adjusted under 35 U.S.C. 154(b) by 167 days.

(21) Appl. No.: 16/453,315

(22) Filed: Jun. 26, 2019

(65) Prior Publication Data
US 2020/0405523 A1 Dec. 31, 2020

(51) Int. Cl.
*A61F 5/445* (2006.01)
*A61B 17/00* (2006.01)
(Continued)

(52) U.S. Cl.
CPC .......... *A61F 5/445* (2013.01); *A61B 17/0057* (2013.01); *A61F 5/4407* (2013.01);
(Continued)

(58) Field of Classification Search
CPC ........ A61F 5/445; A61F 5/4407; A61F 5/448; A61F 5/443; A61F 5/4408;
(Continued)

(56) References Cited

U.S. PATENT DOCUMENTS 3,398,744 A 8/1968 Hooper et al.
5,015,244 A 5/1991 Cross
(Continued)

FOREIGN PATENT DOCUMENTS

EP 3406275 A1 * 11/2018 ....... A61F 13/00068
WO WO-03045492 A1 6/2003
(Continued)

OTHER PUBLICATIONS

Application and File history for U.S. Appl. No. 16/275,029, filed Feb. 13, 2019. Inventors: Obst et al.
(Continued)

*Primary Examiner* — Tatyana Zalukaeva
*Assistant Examiner* — Hans Kaliher
(74) *Attorney, Agent, or Firm* — Patterson Thuente IP (57) ABSTRACT

A skin-safe effluent containment system that may be used to contain fluid leakage from openings in the body of a patient and will adhere to skin in any condition: healthy or injured, wet or dry, smooth, scarred, or uneven. Fluid leakage can occur from natural orifices such as the anus and vagina, spontaneously formed enteric fistulas, rectovaginal fistulas, and surgical openings such as ileostomy and colostomy stomas. The system includes a vacuum-adherent pouch device, comprised of a pouch connected to a porous foam ring which has an air-permeable contact layer on its bottom surface and an air seal on its top surface. The inner and outer perimeters of the foam ring are enclosed and sealed with skin-adhesive materials. When placed on the patient, negative pressure (vacuum) is applied to the foam ring so that the foam collapses and compresses the vacuum-adherent pouch device down against the patient's skin. Negative pressure in combination with the adhesive materials on the perimeters of the foam ring forms a fluid barrier around the opening in the body of the patient so that leakage can be directed into the pouch and drawn away to a separate effluent container.

20 Claims, 12 Drawing Sheets

(51) Int. Cl.
    *A61F 5/44* (2006.01)
    *A61M 25/02* (2006.01)
    *A61F 13/00* (2006.01)
    *A61M 27/00* (2006.01)
    *A61M 39/02* (2006.01)
    *A61N 1/04* (2006.01)
    *A61F 5/448* (2006.01)
    *A61F 5/443* (2006.01)
    *A61M 1/00* (2006.01)

(52) U.S. Cl.
    CPC ... *A61M 25/02* (2013.01); *A61B 2017/00641* (2013.01); *A61F 5/443* (2013.01); *A61F 5/4408* (2013.01); *A61F 5/448* (2013.01); *A61F 13/00068* (2013.01); *A61M 1/90* (2021.05); *A61M 27/00* (2013.01); *A61M 2025/0233* (2013.01); *A61M 2039/027* (2013.01); *A61N 1/0468* (2013.01)

(58) Field of Classification Search
    CPC ...... A61F 13/00068; A61F 5/451; A61F 5/44; A61M 1/0088; A61M 27/00
    See application file for complete search history.

(56) References Cited

U.S. PATENT DOCUMENTS

| | | |
|---|---|---|
| 5,429,626 A | 7/1995 | Fenton |
| 5,636,643 A | 6/1997 | Argenta et al. |
| 5,738,661 A | 4/1998 | Larice |
| 6,099,508 A | 8/2000 | Bousquet |
| 6,709,421 B1 | 3/2004 | Falconer |
| 6,765,122 B1 | 7/2004 | Stout |
| 7,147,627 B2 | 12/2006 | Kim et al. |
| 7,160,275 B2 | 1/2007 | Falconer |
| 7,708,724 B2 | 5/2010 | Weston |
| 8,167,857 B2 * | 5/2012 | James ................ A61M 1/0001 604/319 |
| 8,409,157 B2 | 4/2013 | Haggstrom et al. |
| 8,529,526 B2 | 9/2013 | Wilkes et al. |
| 8,758,314 B2 | 6/2014 | Hall et al. |
| 8,915,894 B1 | 12/2014 | Lonky et al. |
| 9,078,990 B1 | 7/2015 | Obst et al. |
| 9,265,665 B2 | 2/2016 | Robinson et al. |
| 9,629,743 B2 | 4/2017 | Grum-Schwensen |
| 9,782,328 B2 | 10/2017 | Gutwein et al. |
| 10,182,947 B2 | 1/2019 | Hu et al. |
| 10,660,786 B2 | 5/2020 | Obst et al. |
| 2005/0015065 A1 | 1/2005 | Falconer |
| 2007/0191794 A1 | 8/2007 | Cline et al. |
| 2008/0161778 A1 | 7/2008 | Steward |
| 2008/0269700 A1 | 10/2008 | O'Toole et al. |
| 2008/0287892 A1* | 11/2008 | Khan ................ A61M 1/69 604/313 |
| 2008/0319397 A1 | 12/2008 | Macaluso |
| 2009/0131893 A1 | 5/2009 | Priest et al. |
| 2009/0192467 A1 | 7/2009 | Hansen et al. |
| 2009/0209917 A1 | 8/2009 | Tanaka et al. |
| 2009/0227969 A1 | 9/2009 | Jaeb et al. |
| 2010/0145293 A1 | 6/2010 | Verhaalen |
| 2010/0262095 A1 | 10/2010 | Hall |
| 2010/0280489 A1 | 11/2010 | Nishtala et al. |
| 2010/0312192 A1 | 12/2010 | Fitzgerald et al. |
| 2011/0040269 A1 | 2/2011 | Cline |
| 2011/0137270 A1 | 6/2011 | Hu et al. |
| 2011/0213287 A1 | 9/2011 | Lattimore et al. |
| 2012/0029450 A1* | 2/2012 | Grum-Schwensen ........... A61F 5/443 604/344 |
| 2012/0101458 A1 | 4/2012 | Hall et al. |
| 2012/0130187 A1 | 5/2012 | Okoniewski |
| 2012/0232505 A1 | 9/2012 | Eskaros et al. |
| 2014/0148771 A1 | 5/2014 | Luce |
| 2014/0207027 A1 | 7/2014 | Navia et al. |
| 2014/0221946 A1 | 8/2014 | Croizat et al. |
| 2014/0309604 A1 | 10/2014 | Paratore |
| 2014/0324002 A1 | 10/2014 | Luce |
| 2015/0100045 A1 | 4/2015 | Allen et al. |
| 2015/0209492 A1 | 7/2015 | Blott et al. |
| 2016/0120687 A1 | 5/2016 | Obst et al. |
| 2016/0120706 A1 | 5/2016 | Collinson et al. |
| 2016/0287428 A1 | 10/2016 | Eggert et al. |
| 2017/0361069 A1 | 12/2017 | Gazzani Romolo et al. |
| 2017/0367871 A1 | 12/2017 | Dinakara et al. |
| 2019/0046698 A1* | 2/2019 | Loske .................... A61M 1/90 |
| 2020/0253633 A1 | 8/2020 | Obst et al. |

FOREIGN PATENT DOCUMENTS

| | | |
|---|---|---|
| WO | WO-2004084778 A2 | 10/2004 |
| WO | WO 2009/049232 A1 | 4/2009 |
| WO | WO 2010/075032 A2 | 7/2010 |
| WO | WO-2011015203 A1 | 2/2011 |
| WO | WO-2011031822 A1 | 3/2011 |
| WO | WO 2011/138727 A1 | 11/2011 |
| WO | WO 2014/140606 A1 | 9/2014 |
| WO | WO-2019136164 A1 | 7/2019 |

OTHER PUBLICATIONS

Communication dated Jan. 16, 2020 for EP Application No. 15 857 923.5, 5 pages.
Aguila III D.J., et al., "The Stool Shield: A Novel Approach to the Colo-Atmospheric Fistula," Journal of the American College of Surgeons, Sep. 2011, vol. 213 (3), pp. e17-e20.
Byrnes M.C., et al., "A Novel Technique to Skin Graft Abdominal Wall Wounds Surrounding Enterocutaneous Fistulas," Surgical Infections, vol. 11 (6), Apr. 18-20, 2010, pp. 505-510.
Extended European Search Report for Application No. 15857923.5, dated May 2, 2018, 9 pages.
Goverman J., et al., "The "Fistula VAC," a Technique for Management of Enterocutaneous Fistulae Arising within the Open Abdomen: Report of 5 Cases," The Journal of Trauma Injury, Infection, and Critical Care, Feb. 2006, vol. 60 (2), pp. 428-431.
International Preliminary Report on Patentability for Application No. PCT/US2015/058740, dated May 18, 2017, 12 pages.
International Search Report and Written Opinion for Application No. PCT/US2015/058740, dated Feb. 3, 2016, 16 pages.
Stremitzer S., et al., "Successful Bridging Treatment and Healing of Enteric Fistulae by Vacuum-Assisted Closure (VAC) Therapy and Targeted Drainage in Patients with Open Abdomen," International Journal of Colorectal Disease, vol. 26, Jan. 2011, pp. 661-666.
Application and File history for U.S. Appl. No. 13/750,154, filed Jan. 25, 2013. Inventors: Obst et al.
Application and File history for U.S. Appl. No. 14/931,204, filed Nov. 3, 2015. Inventors: Obst et al.
Search Report dated Jul. 14, 2020 for EP Application No. 20157187. 4, 11 pages.
Application and File history for U.S. Appl. No. 16/883,559, filed May 26, 2020, inventors Obst et al.
Application and File history for U.S. Appl. No. 16/453,315, filed Jun. 26, 2019, inventors Obst, et al.

* cited by examiner

ENTERIC FISTULA, RECTOVAGINAL FISTULA, AND OSTOMY EFFLUENT CONTAINMENT SYSTEM, AND DEVICES AND METHODS THEREOF

This disclosure relates to medical devices for use with bodily fluid management systems, and, in particular, to bodily fluid containment systems. This application is related to U.S. patent application Ser. No. 13/750,154, filed Jan. 25, 2013 and entitled "Devices and Methods for Treatment of Fistulas and Complex Wounds," now U.S. Pat. No. 9,078,990, U.S. patent application Ser. No. 14/931,204, filed Nov. 3, 2015 and entitled "Containment Devices for Treatment of Intestinal Fistulas and Complex Wounds," and U.S. patent application Ser. No. 16/275,029, filed Feb. 13, 2019 and entitled "Fluid Management Device for Medical Tubes and Drainage Incisions," all of which are hereby incorporated by reference in their entireties.

TECHNICAL FIELD

Background

Uncontrolled, high-volume leakage of intestinal effluent and fecal matter is a daily challenge for many medical patients with enterocutaneous fistulas (ECF), enteroatmospheric fistulas (EAF), rectovaginal fistulas (RVF), and ostomy stomas. Fluid leakage can occur from natural orifices such as the anus and vagina, spontaneously formed enteric fistulas, and surgical openings such as ileostomy and colostomy stomas. The volume of leakage from a high-output fistula or stoma can range from two to ten or more liters per day, which makes it difficult or impossible for patients to leave their bed and can lengthen hospital stays by weeks or months. In many instances, the leaked fluid causes skin irritation, infection, pain, and feelings of isolation and depression for the patient. Management of such uncontrolled leakage can present many challenges for the patients and healthcare professionals.

A wide range of pouch appliances are available to capture and contain effluent from ostomies and other discharge sites. Example devices that may be used to contain the fluids exiting the body of a patient are described in International Patent Publication No. WO 2011/015203 A1 to Weldingh, International Patent Publication No. WO 2004/0844778 A2 to Ciok, U.S. Patent Publication No. 2008/0269700 A1 to O'Toole, U.S. Pat. No. 5,429,626 to Fenton, and U.S. Pat. No. 5,015,244 to Cross, all of which are incorporated herein by reference in their entireties.

Such devices, however, tend to rely solely on adhesive materials such as hydrocolloids to remain affixed to the patient's skin around the perimeter of the fistula or orifice. These materials do not adhere well when the patient's skin is irritated, weeping, or exuding fluid, uneven due to wounds or scarring, in a moist area of the body, or when they are exposed to constant flows of high-volume effluent. Even with proper placement of such pouch appliances fluid leakage can still occur. There remains a need for an improved containment system.

SUMMARY

This disclosure describes embodiments of a containment system that may be used to contain fluid leakage from openings in the body of a patient. As mentioned above, fluid leakage can occur from natural orifices such as the anus and vagina, spontaneously formed enteric fistulas, rectovaginal fistulas, and surgical openings such as ileostomy and colostomy stomas. As described further below, the components are intended to be used together as a system to address leakage problems that are commonly observed with conventional pouch appliances.

Embodiments are directed to a system which can include a vacuum-adherent pouch device comprising a pouch connected to a porous foam ring which has a skin-safe air-permeable contact layer on its bottom surface and an air seal on its top surface. The inner and outer perimeters of the foam ring are enclosed and sealed with skin-safe adhesive materials. When placed on the patient, negative pressure (i.e. vacuum or near vacuum) is applied to the foam ring, causing the foam to collapse and compress the vacuum-adherent pouch device against the patient's skin forming a seal around the perimeter of the fistula or orifice. Negative pressure in combination with the adhesive materials on the perimeters of the foam ring form a fluid barrier around the opening in the body of the patient so that leakage can be directed into the pouch and drawn away to a separate effluent container, or simply emptied into a toilet.

One embodiment includes a fluid containment system for use in collecting and containing effluent from a bodily orifice. The fluid containment system includes a vacuum-adherent pouch device. The vacuum-adherent pouch device includes a vacuum-adherent base. The vacuum-adherent base further includes a foam wall defining an opening. The foam wall further includes an air permeable lower surface. The foam wall also includes a sealing layer coupled to top and side portions of the foam wall. The sealing layer can form an inner sealing surface and an outer sealing surface. The inner sealing surface and the outer sealing surface can be substantially coplanar with the air permeable lower surface. The inner sealing surface can be formed within the opening of the foam wall and the outer sealing surface formed outside the foam wall. The vacuum-adherent pouch device also includes a pouch configured to collect fluids. The pouch can also include a drain and be coupled to the sealing layer at the inner sealing surface. The vacuum-adherent pouch device also includes a negative pressure coupling configured to fluidly couple a vacuum source to the foam wall. The fluid containment system further includes a negative pressure pump having one or more ports. One of the one or more ports can be coupled to the negative pressure coupling. The fluid containment system further includes an effluent container having one or more effluent ports with one of the one or more effluent ports coupled to the drain.

In one embodiment, the negative pressure pump includes a first port coupled to the negative pressure coupling and a second port coupled to one of the one or more effluent ports of the pouch.

In one embodiment, the effluent container includes a first effluent port coupled to the drain of the pouch and a second effluent port coupled to a vacuum source. The second effluent port can be coupled to a central hospital vacuum line. The second effluent port can be coupled to one of the one or more ports of the negative pressure pump.

In one embodiment, the foam wall of the vacuum-adherent pouch device comprises reticulated foam.

In one embodiment the foam wall forms a ring shape. The foam wall forms a ring shape with an external protrusion or bridge. In this embodiment, the negative pressure coupling fluidly couples to the external protrusion.

In one embodiment, the inner surface and the outer surface of the vacuum-adherent pouch device include a skin adherent. In yet another embodiment, the inner surface of the vacuum-adherent pouch device includes an aperture sized to surround the bodily orifice. The inner surface can be selectively puncturable.

In one embodiment, the air permeable lower surface of the foam wall includes an air permeable skin contact layer.

In embodiments, a tube channel can be formed through one or more portions of the sealing layer and the foam wall.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The present disclosure describes embodiments of a containment system that can be used to contain fluid leakage (e.g., gastric fluid, stool, urine, wound drainage, and the like) from openings in the body of a patient. Fluid leakage can occur from natural orifices such as the anus and vagina, spontaneously formed enteric fistulas, rectovaginal fistulas, and surgical openings such as ileostomy and colostomy stomas. As described in further detail below, the components are intended to be used together as a system to address one or more of the problems outlined above. By way of example, the system components disclosed herein may be used to at least one of create a fluid barrier (e.g., a seal) between the vacuum-adherent pouch device and the skin of the patient, redirect any fluid leakage away from the skin of the patient, and draw leakage to an effluent container. The fluid barrier may substantially or completely prevent the passage of fluid leaking through the points of contact between the vacuum-adherent pouch device and the body of the patient.

Unless otherwise indicated, all numbers expressing feature sizes, amounts, and physical properties are to be understood as being modified by the term "about." Accordingly, unless indicated to the contrary, the numerical parameters set forth are approximations that can vary depending upon the desired properties sought to be obtained by those skilled in the art utilizing the teachings disclosed herein.

As used herein, the singular forms "a", "an", and "the" encompass embodiments having plural referents, unless the content clearly dictates otherwise. As used in this specification and the appended claims, the term "or" is generally employed in its sense including "and/or" unless the content clearly dictates otherwise.

Figure 1:
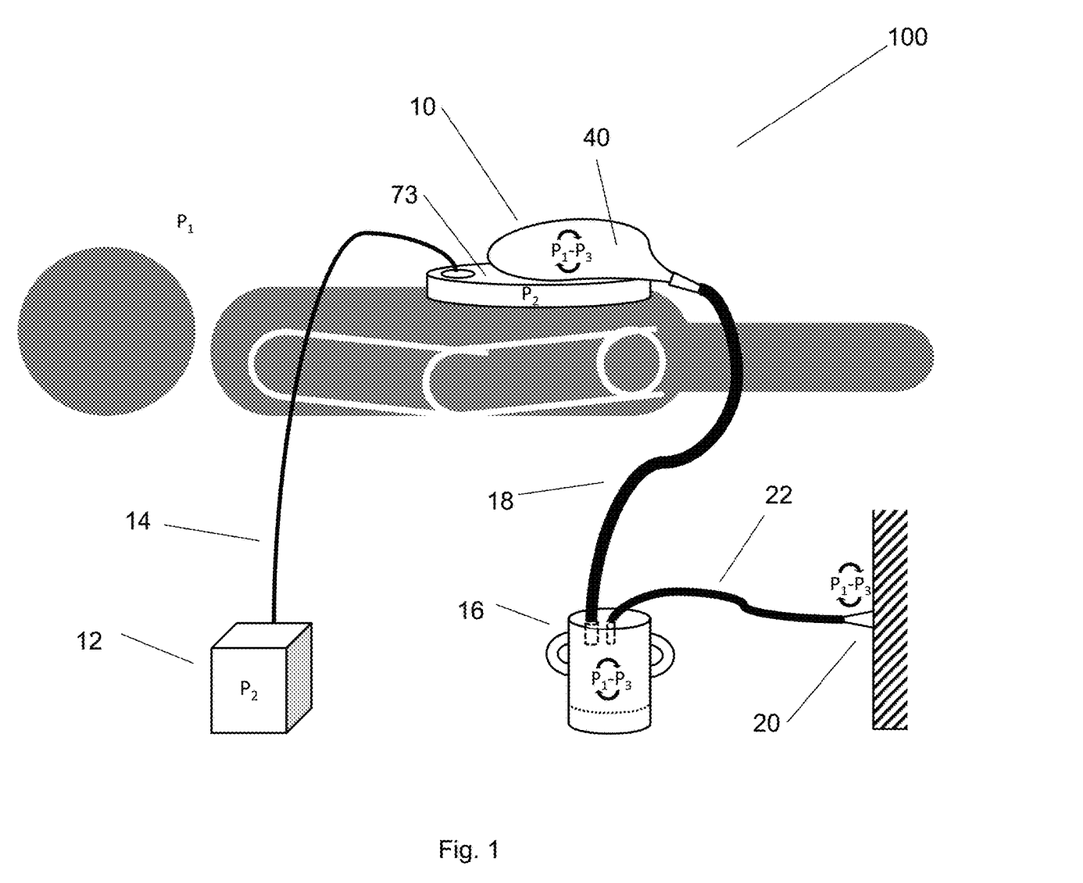
FIG. 1 is a side view of an example of a vacuum-adherent pouch system, according to embodiments described herein.

FIG. 1 depicts an example containment system 100 that is placed on a patient. Containment system 100 includes a vacuum-adherent pouch device 10 connected by an air tube 14 to a negative pressure pump 12. In embodiments, vacuum-adherent pouch device 10 is configured for placement and applied to skin of the patient around the enteric fistula, ostomy, vagina, anus, or other body opening. Vacuum-adherent pouch device 10 also includes a base 73 and a pouch 40.

The pump 12 creates a vacuum pressure $P_2$ less than atmospheric pressure $P_1$ in the base 73 of the vacuum-adherent pouch device 10 to affix it against the patient's skin to create a fluid barrier (e.g., a seal) between the vacuum-adherent pouch device 10 and the skin. The pouch 40 of the vacuum-adherent pouch device 10 is also connected to an effluent container 16 by an effluent drain tube 18. The effluent container 16 is connected by an air tube 22 to hospital wall suction 20. Hospital wall suction 20 is applied intermittently at a pressure $P_3$ less than atmospheric pressure $P_1$ to the effluent container 16 to draw accumulated leakage from the vacuum-adherent pouch device 10 through the effluent drain tube 18 and into the effluent container 16. The design of the effluent container 16 combined with intermittent/cycling of negative pressure allows effluent to be drawn into and retained in the effluent container 16 without fouling the hospital wall suction system 20.

Figure 2:
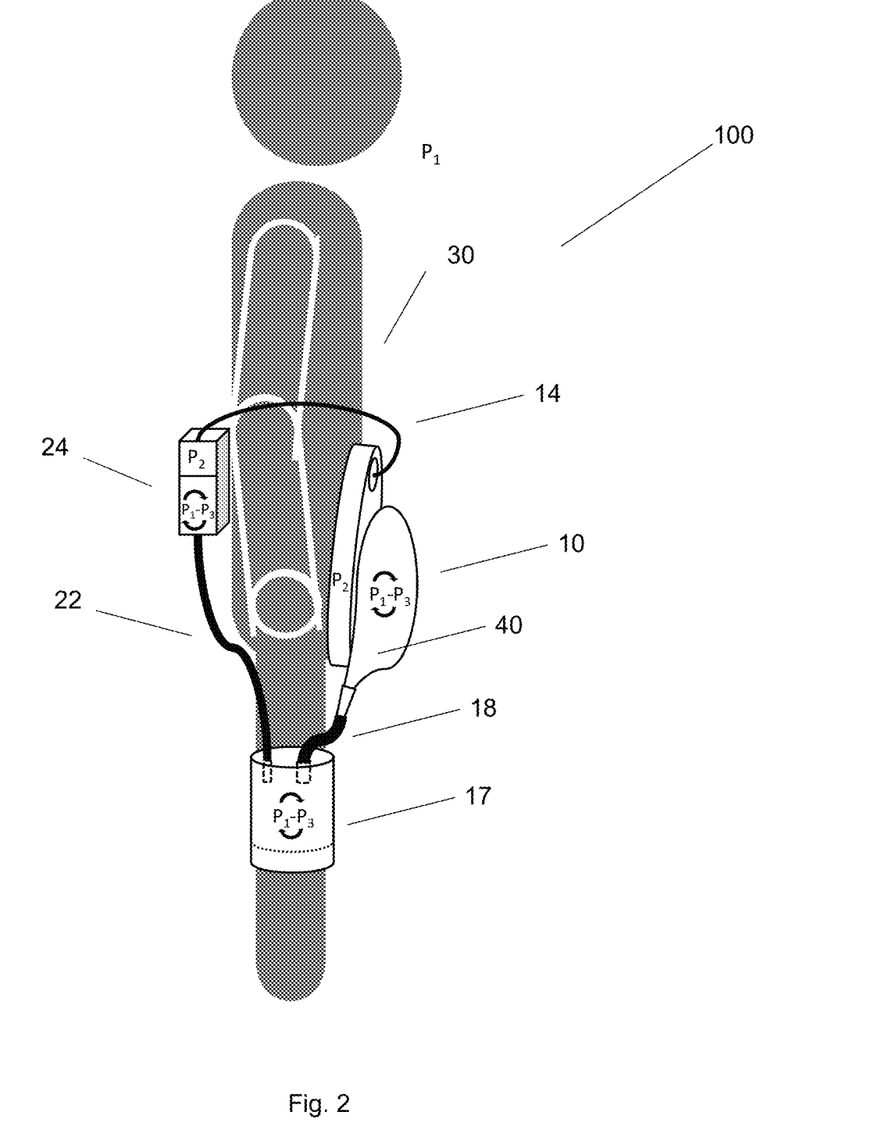
FIG. 2 is a side view of a wearable example of a vacuum-adherent pouch system, according to embodiments described herein.

As depicted in FIG. 2, a wearable example of the containment system 100 is placed on a patient. Containment system 100 includes a vacuum-adherent pouch device 10 connected by air tube 14 to a combination negative pressure and intermittent suction pump 24. Pump 24 creates a vacuum pressure $P_2$ less than atmospheric pressure $P_1$ in base 73 of the vacuum-adherent pouch device 10 to affix it against the patient's skin to create a fluid barrier (e.g., a seal) between the vacuum-adherent pouch device 10 and the skin. The pouch 40 of the vacuum-adherent pouch device 10 is also connected to a wearable effluent container 17 by effluent drain tube 18. The effluent container 17 is connected by air tube 22 to pump 24. Pump 24 applies suction intermittently at a pressure $P_3$ less than atmospheric pressure $P_1$ to the effluent container 17 to draw accumulated leakage from the vacuum-adherent pouch device 10 through the effluent drain tube 18 and into the effluent container 17. The design of the effluent container 17 combined with intermittent/cycling of negative pressure allows effluent to be drawn into and retained in the effluent container 17 without fouling the pump 24.

Figure 3:
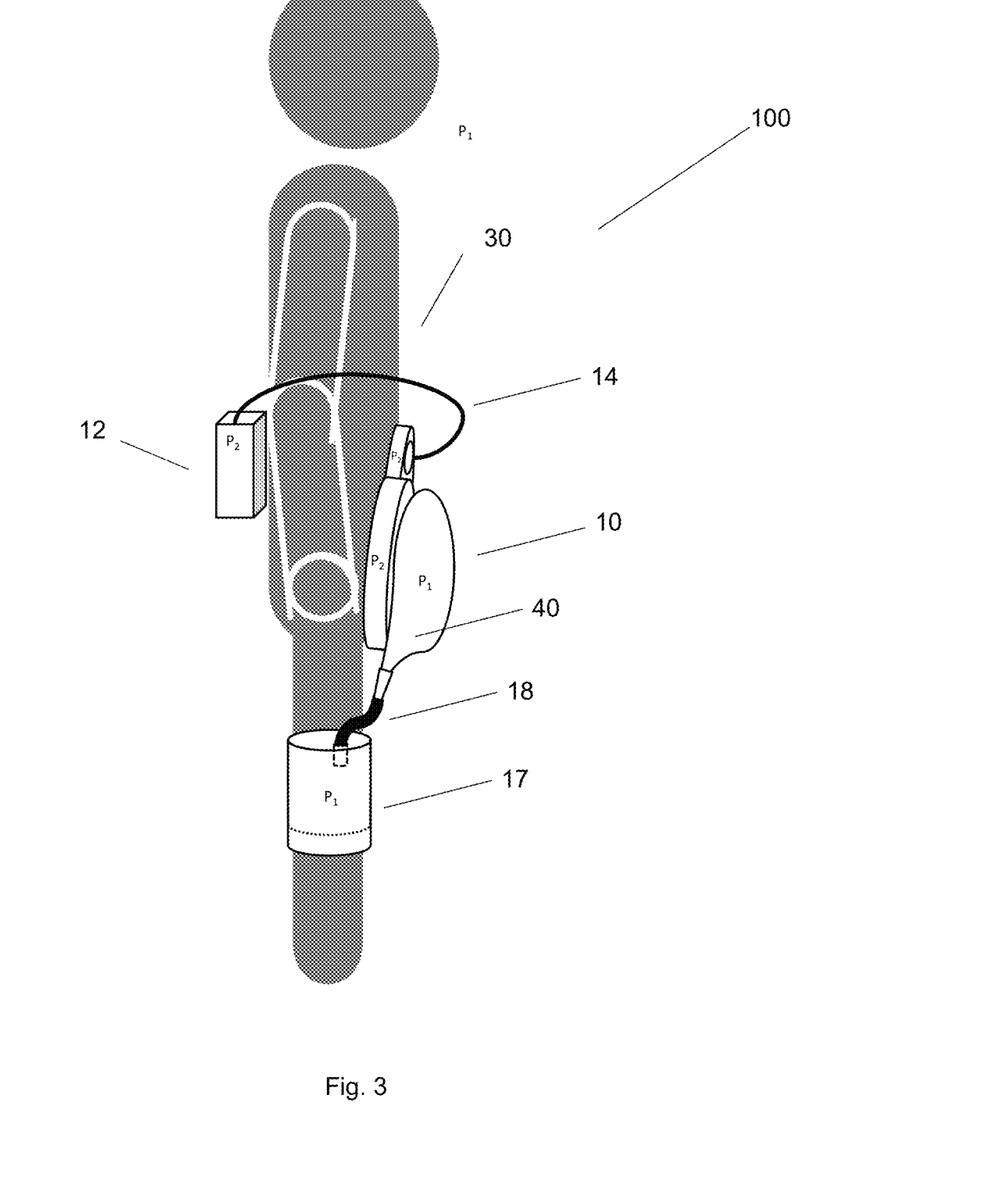
FIG. 3 is a side view of a wearable example of a vacuum-adherent pouch system, according to embodiments described herein.

FIG. 3 illustrates another wearable example of the containment system 100 that is placed on a patient. The system includes vacuum-adherent pouch device 10 connected by air tube 14 to negative pressure pump 12. The pump 12 creates a vacuum pressure $P_2$ less than atmospheric pressure $P_1$ in the base of the vacuum-adherent pouch device 10 to affix it against the patient's skin to create a fluid barrier (e.g., a seal) between the vacuum-adherent pouch device 10 and the skin. Pouch 40 of the vacuum-adherent pouch device 10 is also connected to wearable effluent container 17 by an effluent drain tube 18. Accumulated leakage from the vacuum-adherent pouch device 10 drains by gravity through the effluent drain tube 18 and into the effluent container 17.

Figure 4A:
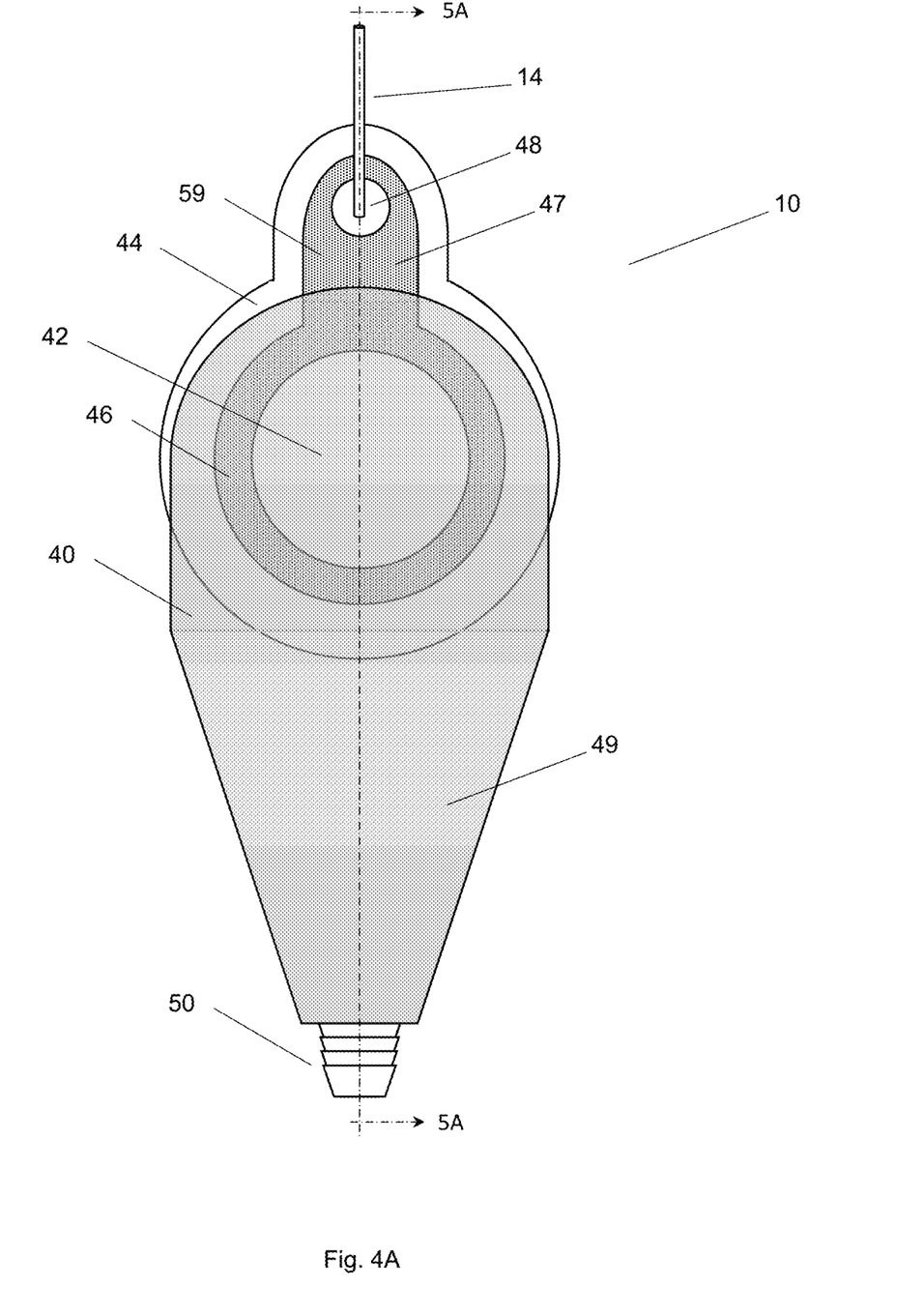
FIG. 4A is a top view of an example vacuum-adherent pouch device, according to embodiments described herein.

FIG. 4A depicts a top view of an embodiment of vacuum-adherent pouch device 10. Vacuum-adherent pouch device 10 includes pouch 40, a reticulated open cell foam ring 46, a reticulated open cell foam bridge 59, a film or other air impermeable material 47 on the top surface of the foam ring 46 and foam bridge 59, a skin-adhesive bottom 42, a skin-adhesive exterior perimeter 44, a negative pressure connector 48, negative pressure air tube 14, a fluid-capture space 49, and an effluent drain connector 50.

The foam bridge 59 is connected to the foam ring 46. The pouch 40 is connected to the foam ring 46. The pouch 40 and the interior perimeter of the foam ring 46 are sealed to the skin-adhesive bottom 42 to form an enclosed fluid-capture space 49. The exterior perimeter of the foam ring 46 and foam bridge 59 are enclosed and sealed with skin-adhesive material 44. The top surface of the foam ring 46 and foam bridge 59 are sealed with a film or other air impermeable material 47 which has a negative pressure connector 48 and air tube 14 attached to supply negative pressure to the foam bridge 59.

To prepare the vacuum-adherent pouch device 10 for application on a patient, a hole is cut in the skin-adhesive bottom 42, sized to fit around the enteric fistula, ostomy, vagina, or other body opening. When the vacuum-adherent pouch device 10 is placed on a patient, the skin-adhesive bottom 42 and the skin-adhesive exterior perimeter 44 form concentric seals between the interior and exterior perimeters of the foam ring 46 and the skin of the patient. Negative pressure is then supplied to the foam ring 46 via the foam bridge 59 and air tube 14 and negative pressure connector 48 to compress the foam ring 46 and affix the vacuum-adherent pouch device 10 to the patient. Fluid leakage is then redirected to the fluid-capture space 49 where it can then be drawn through the effluent drain connector 50 to an effluent container.

Figure 4B:
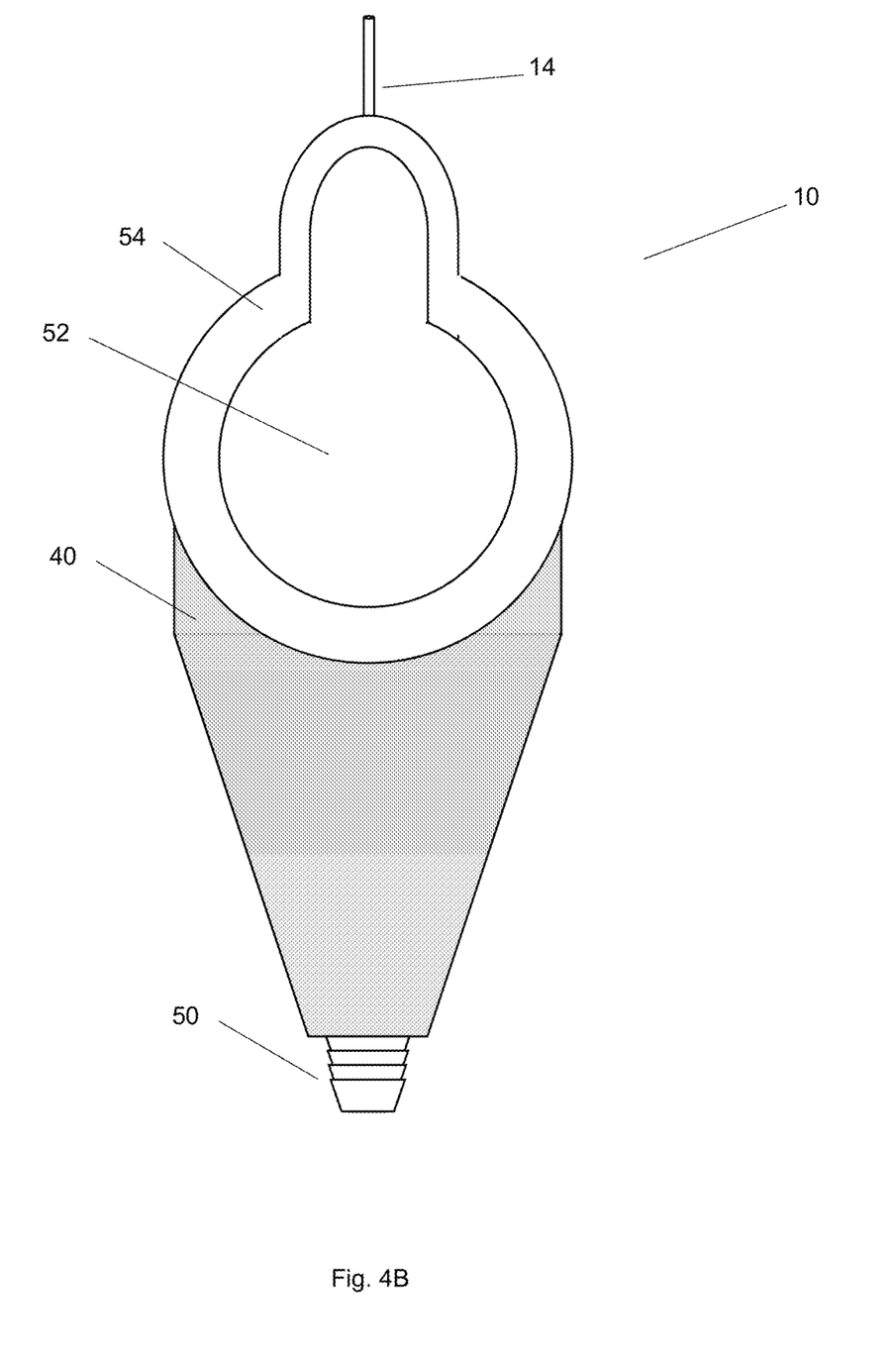
FIG. 4B is a bottom view of an example vacuum-adherent pouch device, according to embodiments described herein.

FIG. 4B depicts a bottom view of an example vacuum-adherent pouch device 10. Vacuum-adherent pouch device 10 includes release paper 52 and release paper 54. Release paper 52 is configured to protect the contact layer and skin-adhesive bottom. Release paper 54 is configured to protect the skin-adhesive exterior perimeter.

To prepare the vacuum-adherent pouch device 10 for application on a patient, a hole is cut through release paper 52 and the skin-adhesive bottom, sized to fit around the enteric fistula, ostomy, vagina, or other body opening. Before the vacuum-adherent pouch device 10 is placed on a patient, release paper 52 is removed to expose the contact layer and skin-adhesive bottom and release paper 54 is removed to expose the skin-adhesive exterior perimeter.

Figure 4C:
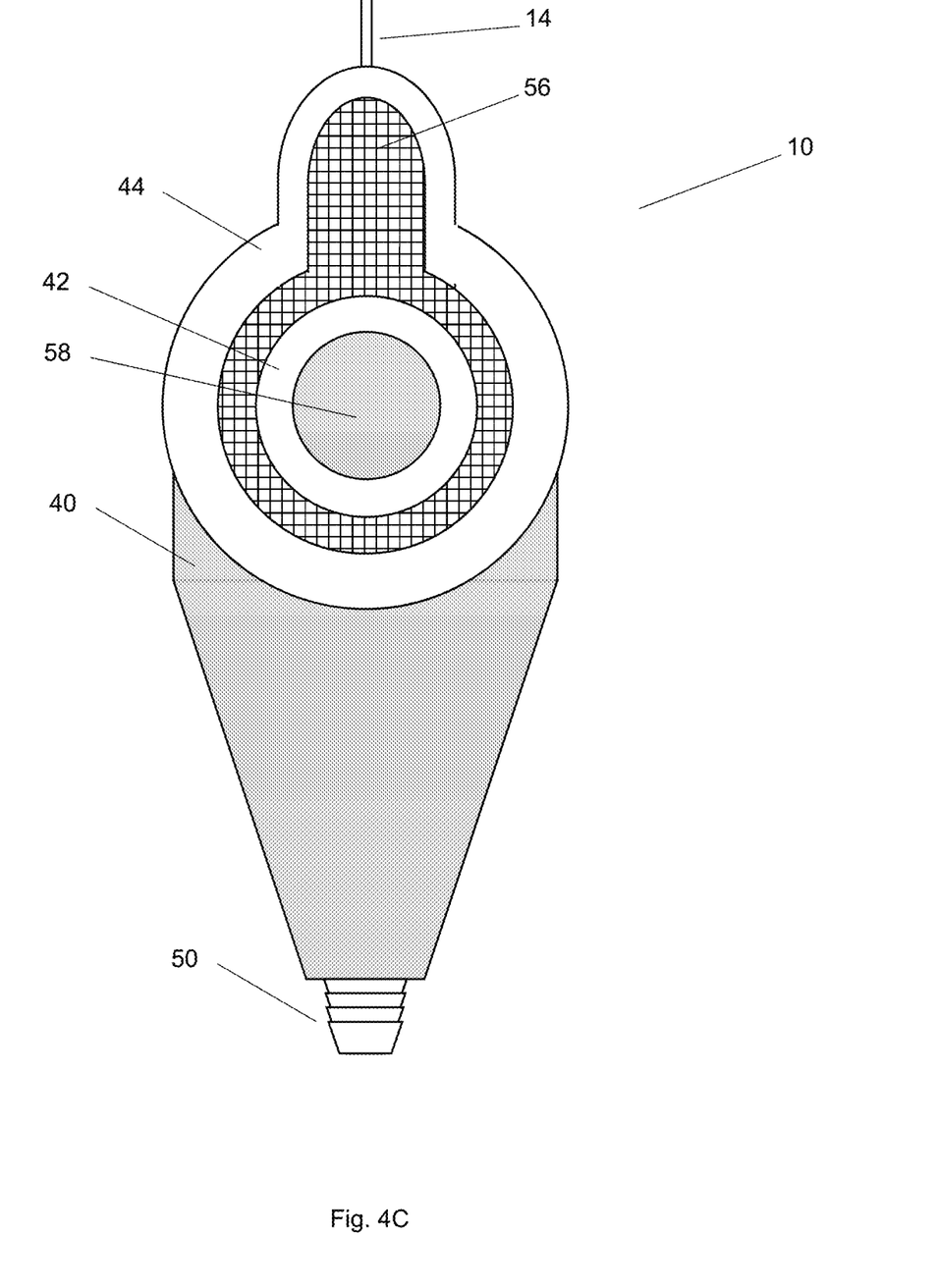
FIG. 4C is a bottom view of an example vacuum-adherent pouch device after it has been prepared for application on a patient, according to embodiments described herein.

FIG. 4C is the bottom view of an example vacuum-adherent pouch device 10 after it has been prepared for application on a patient and includes the skin-adhesive exterior perimeter 44, the air-permeable contact layer 56 on the base of the reticulated open cell foam ring 46 and foam bridge 59, the skin-adhesive bottom 42, and the hole 58 that has been cut in the skin-adhesive bottom 42.

When the vacuum-adherent pouch device 10 is placed on a patient, the hole 58 that has been cut in the skin-adhesive bottom 42 fits around the enteric fistula, ostomy, vagina, or other body opening. The skin-adhesive exterior perimeter 44 and the uncut portion of the skin-adhesive bottom 42 form concentric seals on the skin of the patient. The air-permeable contact layer 56 rests on the skin between concentric skin-adhesives 42 and 44 and protects the skin when negative pressure is supplied to compress the foam ring and foam bridge and affix the vacuum-adherent pouch device 10 to the patient.

Figure 4D:
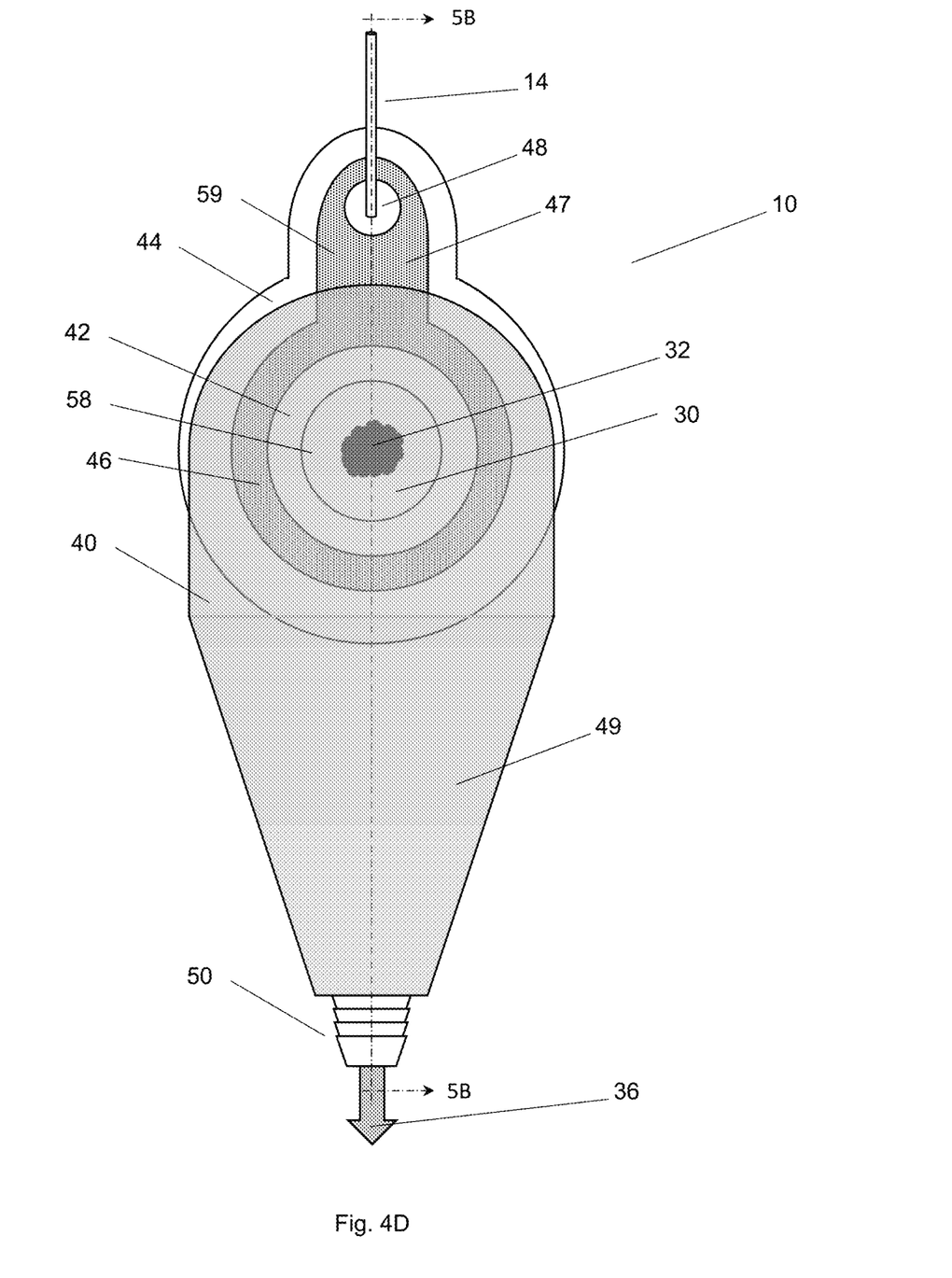
FIG. 4D is a top view of an example vacuum-adherent pouch device after it has been placed on a patient, according to embodiments described herein.

FIG. 4D is a top view of an example vacuum-adherent pouch device 10 after it has been placed on a patient and includes the patient's skin 30, an enteric fistula, ostomy, vagina, or other body opening 32, the pouch 40, the reticulated open cell foam ring 46, the reticulated open cell foam bridge 59, the film or other air impermeable material 47 on the top surface of the foam ring 46 and the foam bridge 59, the skin-adhesive bottom 42, the hole 58 that has been cut in the skin-adhesive bottom 42, the skin-adhesive exterior perimeter 44, the negative pressure connector 48, the negative pressure air tube 14, the fluid-capture space 49, the effluent drain connector 50, and accumulated leakage 36 being drawn from fluid-capture space 49 to an effluent container.

When the vacuum-adherent pouch device 10 is placed on a patient, the hole 58 cut in the skin-adhesive bottom 42 fits around the enteric fistula, ostomy, vagina, or other body opening 32. The skin-adhesive exterior perimeter 44 and the uncut portion of the skin-adhesive bottom 42 form concentric seals on the skin of the patient. Negative pressure is supplied to the foam ring 46 via the foam bridge 59 and air tube 14 and negative pressure connector 48 to compress the film or other air impermeable material 47 and the foam ring 46 and affix the vacuum-adherent pouch device 10 to the patient. Fluid leakage 36 is then redirected to the fluid-capture space 49 where it can then be drawn through the effluent drain connector 50 to an effluent container.

Figure 5A:
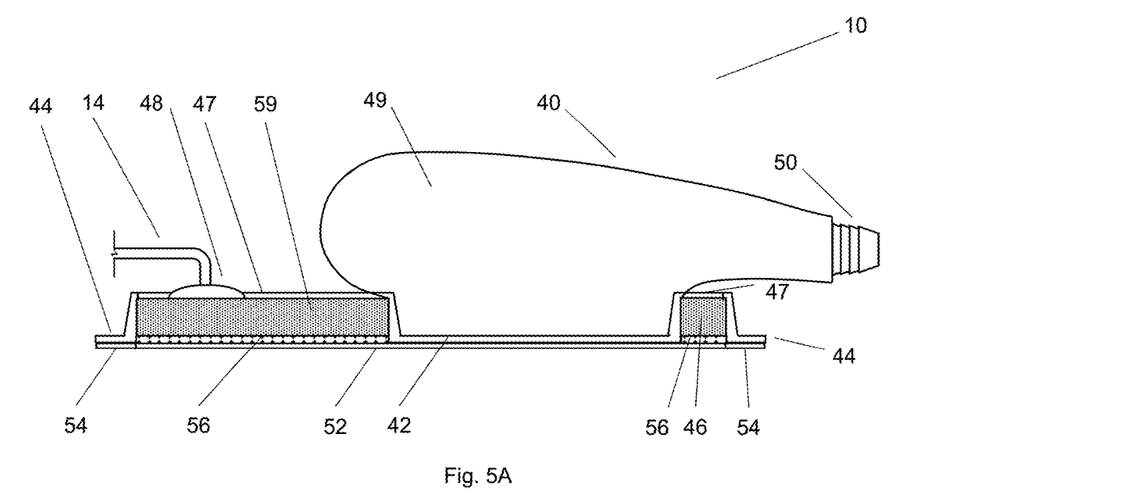
FIG. 5A is a cross-sectional view of the example vacuum-adherent pouch device shown in FIG. 4A, according to embodiments described herein.

FIG. 5A is a cross-sectional view of the example vacuum-adherent pouch device 10 shown in FIG. 4A and includes the pouch 40, the reticulated open cell foam ring 46, the reticulated open cell foam bridge 59, the film or other air impermeable material 47 on the top surface of the foam ring 46 and foam bridge 59, the air-permeable contact layer 56 on the base of the foam ring 46 and foam bridge 59, the skin-adhesive bottom 42, the skin-adhesive exterior perimeter 44, release paper 52 protecting the contact layer and skin-adhesive base 42, release paper 54 protecting the skin-adhesive exterior perimeter, a negative pressure connector 48, a negative pressure air tube 14, the fluid-capture space 49, and the effluent drain connector 50.

The pouch 40 is connected to the foam ring 46. The pouch 40 and the interior perimeter of the foam ring 46 are sealed to the skin-adhesive bottom 42 to form an enclosed fluid-capture space 49. The exterior perimeter of the foam ring 46 and foam bridge 59 are enclosed and sealed with skin-adhesive material 44. The top surface of the foam ring 46 and foam bridge 59 are sealed with a film or other air impermeable material 47 which has a negative pressure connector 48 and air tube 14 attached to supply negative pressure to the foam ring 46. The air-permeable contact layer 56 covers the base of the foam ring 46 and foam bridge 59 and affixes vacuum-adherent pouch device 10 to the patient and also protects the skin when negative pressure is supplied.

Any suitable material may be used to form all or part vacuum-adherent pouch device 10, as will be recognized by those skilled in the art. In some examples, pouch 40 may be formed from one or more biocompatible, sterilizable, materials including, for example, plastics or rubbers. In some examples, foam ring 46 may be formed from one or more biocompatible, sterilizable, materials including, for example, reticulated open cell foam. In some examples, film or other air impermeable material 47 may be formed from one or more biocompatible, sterilizable, materials including, for example, adhesive plastic drape or film. In some examples, air-permeable contact layer 56 may be formed from one or more biocompatible, sterilizable, materials including, for example, non-adherent films, plastics, rubbers, silicones, polyester or other fabrics with pores, slits, or porosities that allow the passage of air. In some examples, skin-adhesive bottom 42 and skin-adhesive exterior perimeter 44 may be formed from one or more biocompatible, sterilizable, materials including, for example, hydrocolloids, silicones, or adhesive plastic drapes or films.

In some examples, vacuum-adherent pouch device 10 may be sterilized for use in a surgical environment. Additionally, or alternatively vacuum-adherent pouch device 10 may be a component of containment system kit that includes vacuum-adherent pouch device 10 which may be sterilized and packaged in a sealed pouch or container that preserves sterility and can be opened by the patient or clinician.

Figure 5B:
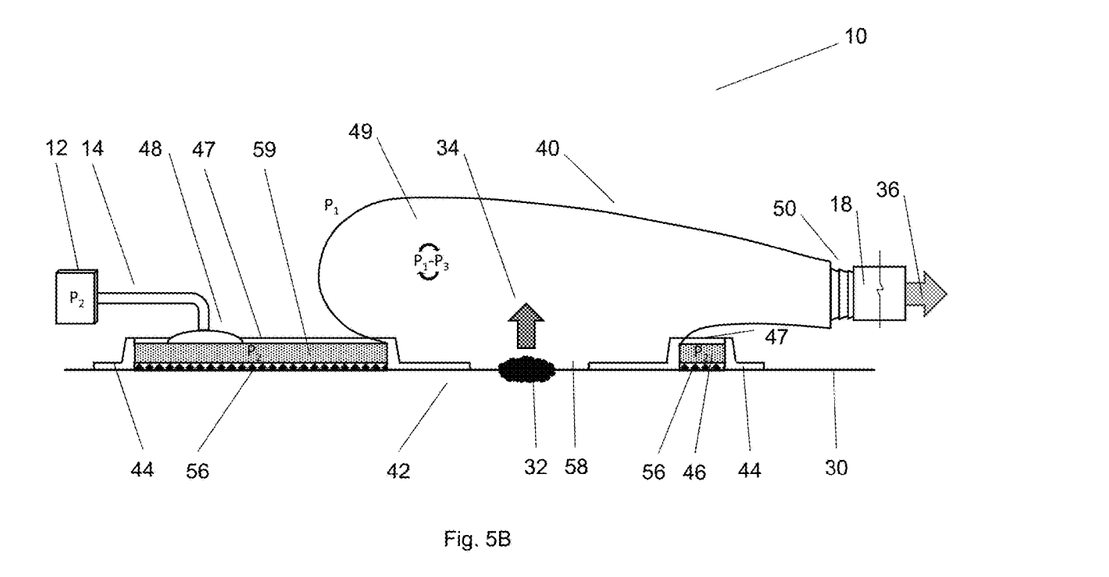
FIG. 5B is a cross-sectional view of the example vacuum-adherent pouch device shown in FIG. 4D, according to embodiments described herein.

FIG. 5B is a cross-sectional view of the example vacuum-adherent pouch device 10 shown in FIG. 4D after it has been placed on a patient and includes the patient's skin 30, an enteric fistula, ostomy, vagina, or other body opening 32, the pouch 40, the reticulated open cell foam ring 46, the reticulated open cell foam bridge 59, the film or other air impermeable material 47 on the top surface of the foam ring 46 and foam bridge 59, the air-permeable contact layer 56 on the base of the foam ring 46 and foam bridge 59, the skin-adhesive bottom 42, the hole 58 that has been cut in the skin-adhesive bottom 42, the skin-adhesive exterior perimeter 44, the negative pressure connector 48, the negative pressure air tube 14, the negative pressure pump 12, the fluid-capture space 49, intestinal and other bodily fluid effluent 34, an effluent drain connector 50, the effluent drain tube 18, and accumulated leakage 36 being drawn from fluid-capture space 49 to an effluent container.

When the vacuum-adherent pouch device 10 is placed on a patient, the hole 58 is cut in the skin-adhesive bottom 42 to fit around the enteric fistula, ostomy, vagina, or other body opening 32. The skin-adhesive exterior perimeter 44 and the uncut portion of the skin-adhesive bottom 42 form concentric seals on the skin of the patient. Negative pressure is supplied to the foam ring 46 from the negative pressure pump 12 via foam bridge 59 and the air tube 14 and negative pressure connector 48 to compress the foam ring 46 and the surface film or other air impermeable material 47. The air-permeable contact layer 56 covers the base of the foam ring 46 and foam bridge 59 and affixes vacuum-adherent pouch device 10 to the patient and also protects the skin. Intestinal and other bodily fluid effluent 34 from the enteric fistula, ostomy, vagina, or other body opening is directed to the fluid-capture space 49. Accumulated leakage 36 is drawn through the effluent drain connector 50 and effluent drain tube 18 to an effluent container.

Figure 5C:
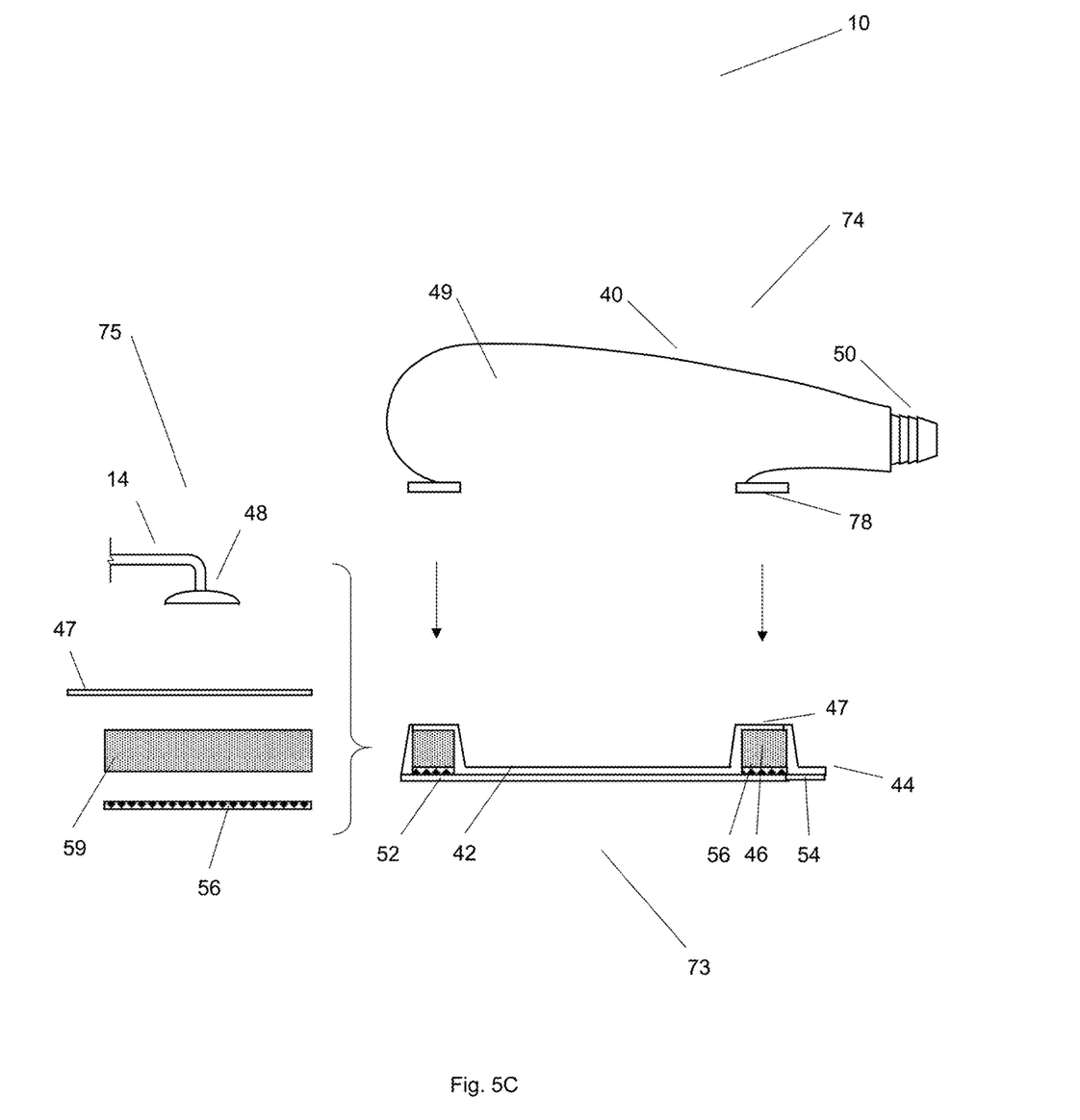
FIG. 5C is an exploded view of the example vacuum-adherent pouch device shown in FIG. 5A showing device subcomponent options, according to embodiments described herein.

FIG. 5C is a view of the example vacuum-adherent pouch device shown in FIG. 5A showing device subcomponent options. Vacuum-adherent pouch device 10 may be provided for use in whole or as subcomponents for assembly at the bedside as will be recognized by those skilled in the art. For example, vacuum-adherent base subcomponent 73 and pouch subcomponent 74 may be fastened together with an adhesive ring 78. A bridge to provide negative pressure to vacuum-adherent base subcomponent 73 may be formed by assembling air-permeable skin contact layer 56, the reticulated open cell foam bridge 59, film or other air impermeable material 47, and negative pressure attachment subcomponent 75. These or other subcomponents may be assembled when the vacuum-adherent pouch device 10 is placed on the patient.

Figure 6A:
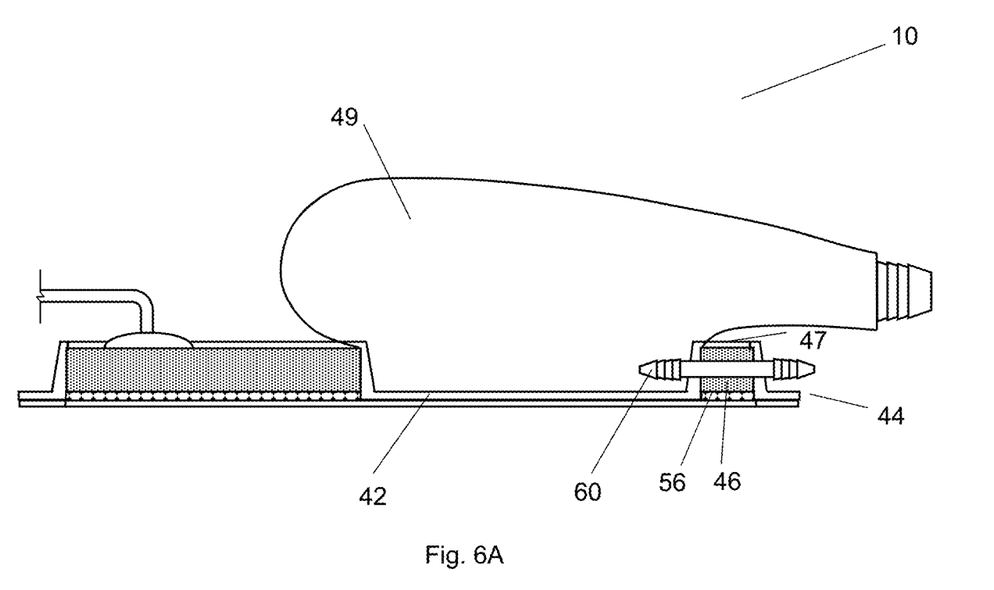
FIGS. 6A and 6B are cross-section views of an example vacuum-adherent pouch device illustrating example options for passing fistuloclysis and other tubes through the vacuum-adherent pouch device, according to embodiments described herein.
Figure 6B:
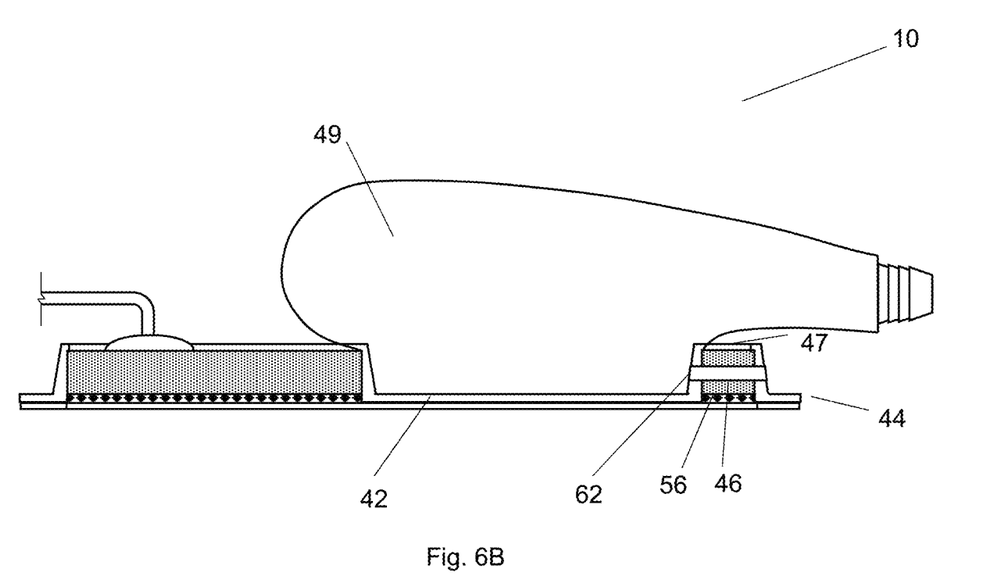

FIGS. 6A and 6B show examples of a vacuum-adherent pouch device 10 that include an optional feature to enable passage of fistuloclysis (fistula feeding), catheter, and other tubes for the purpose of transporting fluids into or out of the enteric fistula, ostomy, vagina, or other body opening. FIG. 6A illustrates a cross-sectional view of an example vacuum-adherent pouch device 10 with a tube connector 60 for splicing a tube into the fluid-capture space 49. FIG. 6B illustrates a cross-sectional view of an example vacuum-adherent pouch device 10 with a tube channel 62 for passing a tube into the fluid-capture space 49. Preferably, tube connector 60 and tube channel 62 are formed using a non-fluid permeable and/or non-porous flexible material. Further, as will be recognized by those skilled in the art, the tube connector 60 and tube channel 62 can be sized and shaped to accommodate all different sizes and shapes medical tubes.

Figure 7A:
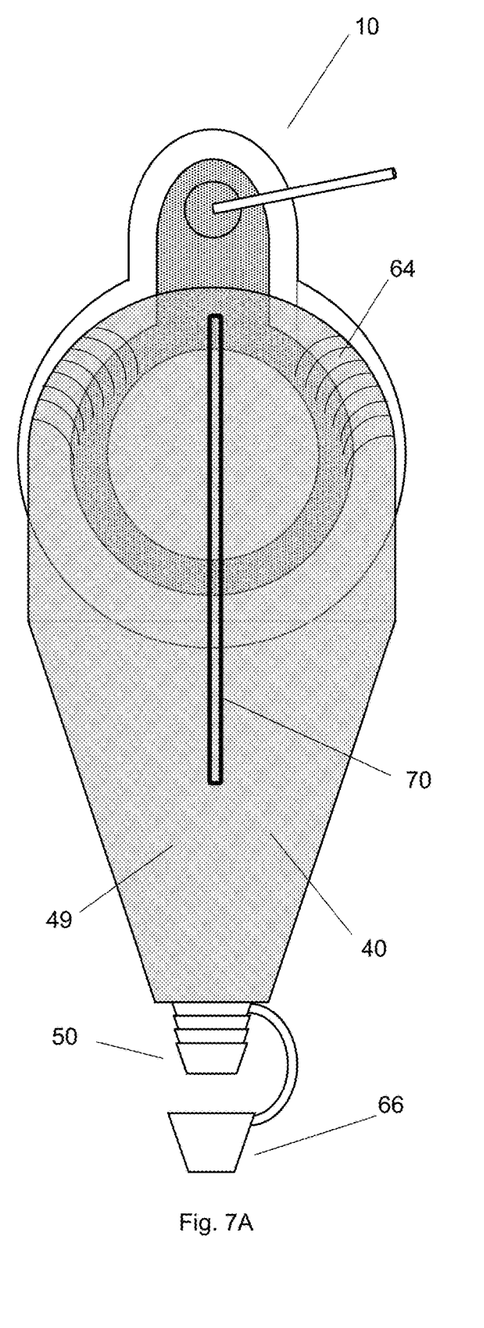
FIGS. 7A and 7B are top-views of alternative embodiments of a vacuum-adherent pouch device, according to embodiments described herein.
Figure 7B:
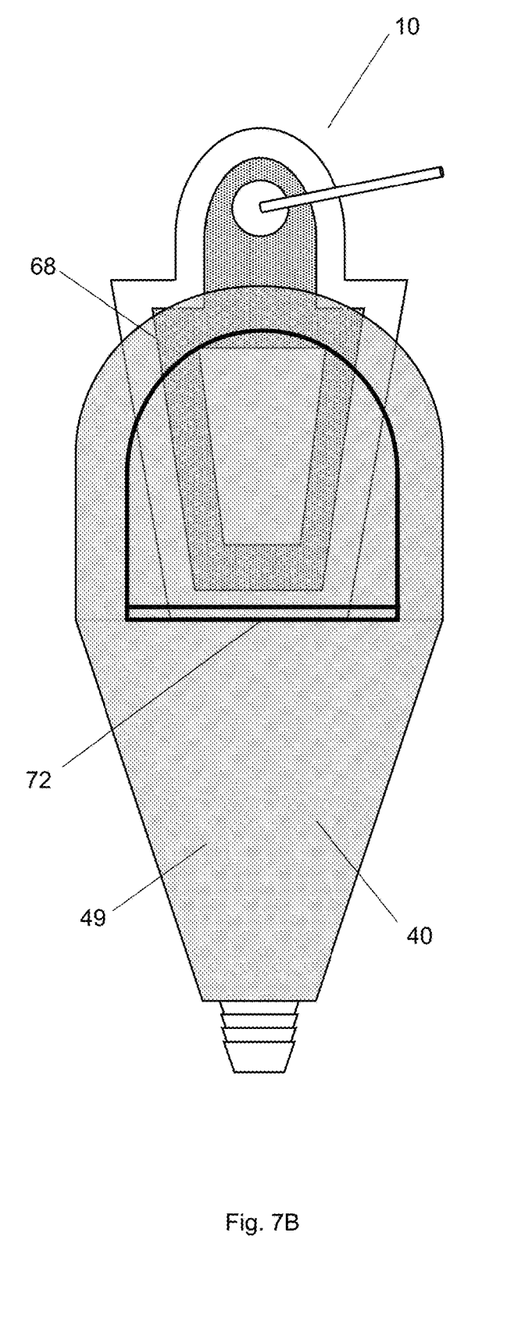

The vacuum-adherent pouch device 10 may include any or all of the following optional features shown and described with respect to the additional examples of FIGS. 7A and 7B. The features disclosed and described in the context of FIGS. 4A to 6B may be used in combination with any of the other features described herein such that it will be understood that any feature or specific combination of features shown in the accompanying figures is not intended to be limited to only the specific embodiments illustrated.

The example vacuum-adherent pouch device 10 illustrated in FIG. 7A includes bellows or pleats 64 in the pouch 40 to enable expansion of the vacuum-adherent pouch device 10 to fit larger body openings, an effluent drain connector cap 66 which is integral to the effluent drain connector 50 and snaps onto the effluent drain connector 50 to seal the fluid-capture space 49, and a resealable zip-type opening 70 to access the fluid-capture space 49.

The example vacuum-adherent pouch device 10 illustrated in FIG. 7B includes a resealable lid opening 72 to access the fluid-capture space 49, and an alternative form factor 68 to fit the perineal area. Further, as will be recognized by those skilled in the art, the vacuum-adherent pouch device 10 can be sized and shaped to accommodate all different sizes and shapes of patients and body openings.

Figure 8:
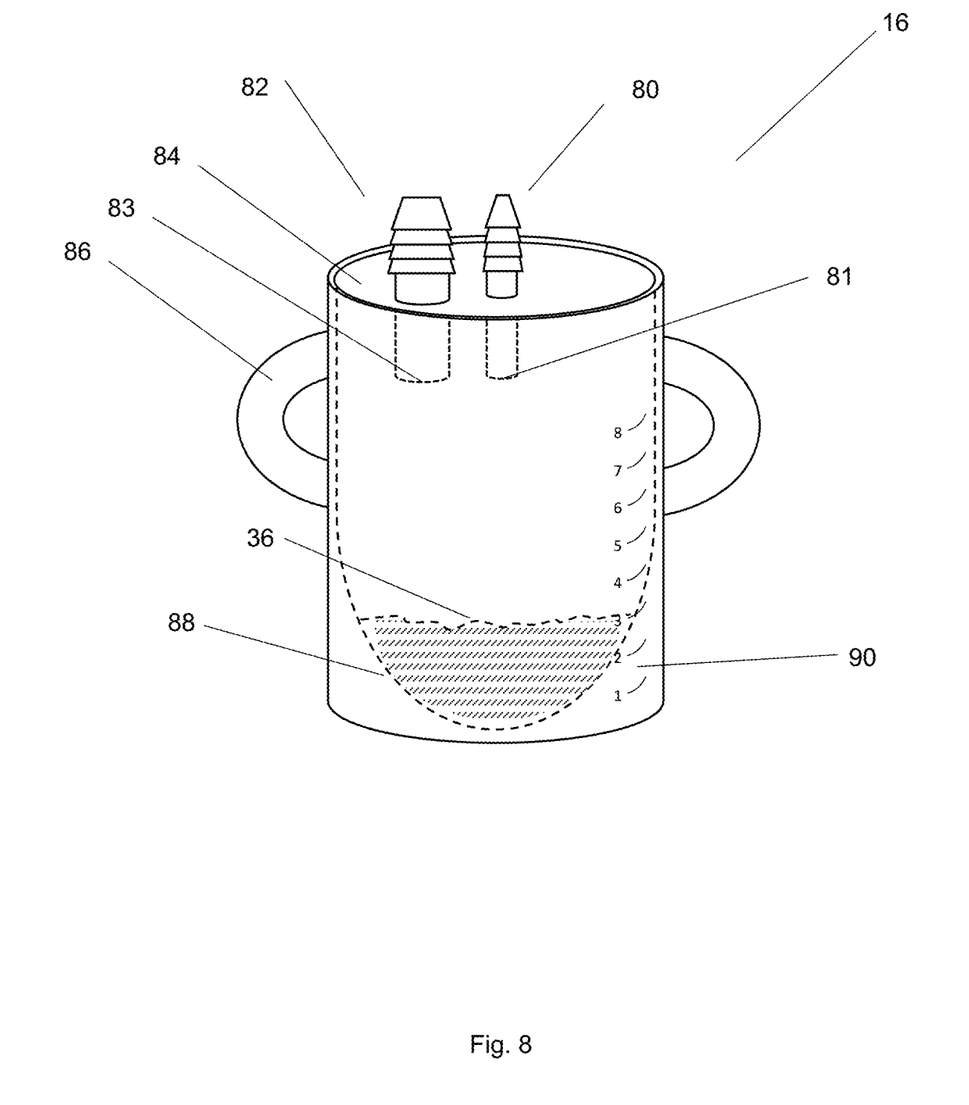
FIG. 8 is an isometric view of an example effluent container, according to embodiments described herein.

FIG. 8 illustrates an example effluent container 16 and includes an intermittent negative pressure connector 80 with a vacuum port 81 inside the container 16, an effluent container connector 82 with an effluent port 83 inside the container 16, a resealable lid 84, carrying handle(s) 86, a water proof liner 88, and fluid measurement marks 90 on the exterior of the effluent container 16.

When the containment system is placed on a patient, the effluent container 16 is connected to intermittent suction via the intermittent negative pressure connector 80, and to the vacuum-adherent pouch device via the effluent container connector 82. When intermittent suction is applied to the effluent container 16, negative pressure draws accumulated leakage 36 from the vacuum-adherent pouch device into the effluent container 16 through the effluent port 83.

The effluent port 83 and the vacuum port 81 are separated from each other near the top of the container 16 so that leakage 36 that is drawn into the effluent container 16 falls to the bottom of the container 16. The separation of the effluent port 83 from the vacuum port 81 and the application of intermittent or cycling negative pressure prevents effluent from being drawn into the vacuum port 81 where it may foul the intermittent negative pressure pump.

The effluent container 16 may include any or all of the following optional features including a resealable lid 84 for use in dumping the effluent container 16 when full of leakage 36, carrying handle(s) 86 for use in carrying the effluent container 16, a disposable water proof liner 88 as an alternative to dumping and cleaning the effluent container 16, and fluid measurement marks 90 on the walls of the effluent container 16 to measure the output of enteric fistulas, rectovaginal fistulas, and ostomy stomas.

Preferably, effluent container 16 is formed using a non-fluid permeable and/or non-porous flexible material which is transparent or translucent so the volume level of accumulated leakage 36 can be seen through the walls of the effluent container 16. Further, as will be recognized by those skilled in the art, the effluent container 16 can be sized and shaped to accommodate all different effluent volumes and use scenarios to include hospital, in-home, and wearable.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A vacuum-adherent pouch device for use in a fluid containment system for use in collecting and containing effluent from a bodily orifice, the vacuum-adherent pouch device comprising:
   a vacuum-adherent base including:
   a collapsible foam wall including structure defining an opening,
   an air permeable, skin-safe contact layer coupled to a bottom surface of the foam wall,
   an air impermeable layer coupled to a top surface of the foam wall,
   a first adhesive layer extending inwardly from an inner perimeter of the foam wall to cover the opening in the foam wall, and
   a second adhesive layer extending outwardly from an outer perimeter of the foam wall at the bottom surface thereof,
   the first adhesive layer and the second adhesive layer being substantially coplanar with the air permeable lower surface,
   wherein the first adhesive layer is configured to be punctured or cut in a region proximate the bodily orifice, thereby forming an aperture sized to surround the bodily orifice;
   a pouch configured to collect fluids, the pouch further including a drain, the pouch coupled to the foam wall and over the opening; and
   a negative pressure coupling configured to fluidly couple a vacuum source to the device, wherein the foam wall is configured to collapse upon application of the vacuum source to seal the pouch over the bodily orifice for collection of effluent therefrom.

2. The vacuum-adherent pouch device of claim 1, wherein the foam wall comprises reticulated foam.

3. The vacuum-adherent pouch device of claim 1, wherein the foam wall forms a ring shape.

4. The vacuum-adherent pouch device of claim 1, wherein the foam wall forms a ring shape with an external protrusion.

5. The vacuum-adherent pouch device of claim 4, wherein the negative pressure coupling fluidly couples to the external protrusion.

6. The vacuum-adherent pouch device of claim 1, wherein the first and second adhesive layers include a skin adherent.

7. The vacuum-adherent pouch device of claim 1, wherein the first adhesive layer includes an aperture sized to surround the bodily orifice.

8. The vacuum-adherent pouch device of claim 1, wherein the first adhesive layer is selectively puncturable.

9. The vacuum-adherent pouch device of claim 1, wherein a tube channel is formed through one or more portions of the foam wall.

10. A fluid containment system for use in collecting and containing effluent from a bodily orifice, the fluid containment system comprising:
   a vacuum-adherent pouch device of claim 1;
   a negative pressure pump having one or more ports, one of the one or more ports coupled to the negative pressure coupling; and
   an effluent container having one or more effluent ports, one of the one or more effluent ports coupled to the drain.

11. The system of claim 10, wherein the negative pressure pump includes a first port coupled to the negative pressure coupling and a second port coupled to one of the one or more effluent ports of the effluent container.

12. The system of claim 10, wherein the effluent container includes a first effluent port coupled to the drain of the pouch and a second effluent port coupled to a vacuum source.

13. The system of claim 12, wherein the second effluent port is coupled to a central hospital vacuum line.

14. The system of claim 12, wherein the second effluent port is coupled to one of the one or more ports of the negative pressure pump.

15. The system of claim 10, wherein the foam wall forms a ring shape with an external protrusion.

16. The system of claim 15, wherein the negative pressure coupling fluidly couples to the external protrusion.

17. The system of claim 10, wherein the first and second adhesives include a skin adherent.

18. The system of claim 10, wherein the first adhesive layer includes an aperture sized to surround the bodily orifice.

19. The system of claim 10, wherein a tube channel is formed through one or more portions of the foam wall.

20. The vacuum-adherent pouch device of claim 1, wherein the vacuum-adherent base is configured to entirely collapse to compress and seal the pouch over the bodily orifice.

* * * * *